(12) United States Patent
Brandt et al.

(10) Patent No.: US 8,151,644 B2
(45) Date of Patent: Apr. 10, 2012

(54) METHOD AND APPARATUS OF DETECTING AN OBJECT

(75) Inventors: Robert Kurt Brandt, Hubertus, WI (US); Mark Stephen Williamsen, Milwaukee, WI (US)

(73) Assignee: Brandt Innovative Technologies, Inc., Pewaukee, WI (US)

( * ) Notice: Subject to any disclaimer, the term of this patent is extended or adjusted under 35 U.S.C. 154(b) by 657 days.

(21) Appl. No.: 11/913,414

(22) PCT Filed: May 4, 2006

(86) PCT No.: PCT/US2006/016822
§ 371 (c)(1),
(2), (4) Date: May 20, 2008

(87) PCT Pub. No.: WO2007/070080
PCT Pub. Date: Jun. 21, 2007

(65) Prior Publication Data
US 2008/0289427 A1    Nov. 27, 2008

Related U.S. Application Data

(60) Provisional application No. 60/677,751, filed on May 4, 2005.

(51) Int. Cl.
*G01N 29/24* (2006.01)
*G01N 29/06* (2006.01)
(52) U.S. Cl. ........................................... 73/643
(58) Field of Classification Search ............. 73/643, 73/655–657, 601
See application file for complete search history.

(56) References Cited

U.S. PATENT DOCUMENTS

| | | | |
|---|---|---|---|
| 4,455,268 | A | 6/1984 | Hinrichs et al. |
| 4,543,486 | A | 9/1985 | Rose |
| 4,567,769 | A | 2/1986 | Barkhoudarian |
| 4,758,803 | A | 7/1988 | Thomas, III |
| 4,862,384 | A | 8/1989 | Bujard |
| 5,505,090 | A | 4/1996 | Webster |
| 5,533,339 | A | 7/1996 | Clare et al. |

(Continued)

FOREIGN PATENT DOCUMENTS

JP            61120041        6/1986

(Continued)

OTHER PUBLICATIONS

Shih, Frank, J., et al., "Determination of Glass Thickness Using Laser-Based Ultrasound", CP557, Review of Progress in Quantitative Evaluation, vol. 20, pp. 287-292, 1-56396-988-2/01, 2001 American Institute of Physics.

(Continued)

*Primary Examiner* — Hezron E Williams
*Assistant Examiner* — Rose M Miller
(74) *Attorney, Agent, or Firm* — Michael Best & Friedrich LLP

(57) ABSTRACT

A portable non-contact sensor system including a laser generator subsystem, a laser detector subsystem, a beam steering subsystem, an analysis subsystem, a power management subsystem, a user interface, and a communications interface. The laser generator subsystem is configured to project a plurality of laser pulses at a surface of an object that is to be characterized. The laser detector subsystem is configured to receive return laser pulses from the object. The analysis subsystem is configured to analyze the received return pulses and characterize the object.

24 Claims, 14 Drawing Sheets

U.S. PATENT DOCUMENTS

| | | | |
|---|---|---|---|
| 5,672,830 A * | 9/1997 | Rogers et al. | 73/597 |
| 5,698,787 A | 12/1997 | Parzuchowski et al. | |
| 5,801,312 A | 9/1998 | Lorraine et al. | |
| 5,821,424 A | 10/1998 | Rodriguez | |
| 5,886,264 A | 3/1999 | Hu et al. | |
| 5,929,337 A | 7/1999 | Collins et al. | |
| 5,982,482 A * | 11/1999 | Nelson et al. | 356/237.1 |
| 6,029,520 A | 2/2000 | Beall et al. | |
| 6,182,512 B1 | 2/2001 | Lorraine | |
| 6,186,004 B1 | 2/2001 | Kaduchak et al. | |
| 6,234,023 B1 | 5/2001 | Collins et al. | |
| 6,518,584 B1 | 2/2003 | Woodruff | |
| 6,595,059 B2 | 7/2003 | Gorman et al. | |
| 6,668,654 B2 * | 12/2003 | Dubois et al. | 73/643 |
| 6,856,918 B2 | 2/2005 | Dubois et al. | |
| 6,938,488 B2 | 9/2005 | Diaz et al. | |
| 2002/0100884 A1 * | 8/2002 | Maddock | 250/559.29 |
| 2002/0121602 A1 * | 9/2002 | Thomas et al. | 250/341.6 |
| 2006/0169029 A1 * | 8/2006 | Heyman | 73/52 |

FOREIGN PATENT DOCUMENTS

| | | |
|---|---|---|
| JP | 03282253 | 12/1991 |
| JP | 04286933 | 10/1992 |
| JP | 10277035 | 10/1998 |
| JP | 11083433 | 3/1999 |
| JP | 2002028793 | 1/2002 |
| JP | 2005536726 | 12/2005 |
| WO | 0014521 | 3/2000 |
| WO | 01/14825 | 3/2001 |
| WO | 03/089955 | 10/2003 |
| WO | 2007070080 | 6/2007 |

OTHER PUBLICATIONS

MetroLaser, Inc., VibroMet 500.

O'Melveny, Sean, "Diet Coke or Chemicals?: Sensor Outsmarts Smugglers", copyright 2005 Military.com.

R&D, Features, What's in That Tanker Truck?, Reed Business Information, Science & Medical Group, copyright 2003 R&D.

"Detector Can Scan Containers for Contraband Without Unsealing", Aviation Week's Homeland Security & Defense, Feb. 20, 2003.

Quarktet, Research, available online at: <http://www.quarktet.com/Research.html>, available at least as early as Jul. 10, 2005.

Rivera, Ray, "NW Tool Enlisted in Iraq Search", The Seattle Times, Mar. 14, 2003.

Martin, Froeschner & Associates All Fiber Doppler Velocity Interferometer (VISAR) Systems, updated Jun. 2004.

Dantec Dynamics, About the Dantec Dynamics Group, Laser Optical Measurement Systems and Sensors, Publication No. 214_v1, 2000 certified.

Brüel & Kjaer, Quality Control Laser Doppler Vibrometer—Type 8337, Product Data, BP2056-11, Apr. 2007.

Lasson Technologies, "Lasson Technologies Introduces the AIR-1550-TWM Laser Ultrasonic Receiver for Non-Destructive Testing", Press Release, 2005.

Holland, Jesse, J., "Anti-Terrorism Fight Goes High-Tech", washingtonpost.com, Mar. 5, 2002.

Polytec, Laser Vibrometers—Solutions for Every Vibration Measurement Need, Product Flyer, 2004.

Ing, R.K., et al., "Ultrasonic Detection on Rough Surfaces Using Heterodyne Photorefractive Interferometer: Applications to NDE", IEEE Ultrasonic Symposium, pgs. 681-684, 1996.

Atherton, Kathryn, et al., "Generation and Detection of Broadband Laser Generated Ultrasound From Low Power Laser Sources", Photonics 2000: International Conference on Fiber Optics and Photonics, Proceedings of SPIE, vol. 4417, pp. 19-32, 2001.

Blouin, Alain, et al., "Detection of Ultrasonic Motion of a Scattering Surface by Two-Wave Mixing in a Photorefractive GaAs Crystal", Applied Physics Letters, vol. 65, No. 8, pp. 932-934, Aug. 22, 1994.

Campagne, Benjamin, et al., "Compact and Fast Response Ultrasonic Detection Device Based on Two-Wave Mixing in a Gallium Arsenide Photorefractive Crystal", Review of Scientific Instruments, vol. 72, No. 5, pp. 2478-2482, May 2001.

Delaye, Philippe, "Heterodyne Detection of Ultrasound From Rough Surfaces Using a Double Phase Conjugate Mirror", Applied Physics Letters, vol. 67, No. 22, pp. 3251-3253, Nov. 27, 1995.

Delaye, Philippe, et al., "Detection of Ultrasonic Motion of Scattering Surface by Photorefractive InP:Fe Under an Applied dc Field", J. Opt. Soc, Am. B, vol. 14, No. 7, pp. 1723-1734, Jul. 1997.

Glass, A.M., et al., "Four-Wave Mixing in Semi-Insulating InP and GaAs Using the Photorefractive Effect", Applied Physics Letters, vol. 44, No. 10, pp. 948-950, May 15, 1984.

Golovan, L.A., et al., "Efficient Nonlinear Optical Conversion in Porous GaP—The Effect of Light Localization", Photonic Crystal Materials and Devices II, Proceeding of SPIE, vol. 5360, pp. 333-338, 2004.

Honda, Tokuyuki, et al., "Optical Measurement of Ultrasonic Nanometer Motion of Rough Surface by Two-Wave Mixing in Bi12SiO20", Jpn. J. Appl. Phys., vol. 34, part 1, No. 7A, pp. 3737-3740, Jul. 1995.

Iida, Yasuhiro, et al., "Detection of Small In-Plane Vibrations Using the Polarization Self-Modulation Effect in GaP",.Journal of Optics A: Pure and Applied Optics, vol. 5, pp. S457-S461, 2003.

Ing, R.K, et al., "Broadband Optical Detection of Ultrasound by Two-Wave Mixing in a Photorefractive Crystal", Applied Physics Letters, vol. 59, No. 25, pp. 3233-3235, Dec. 16, 1991.

Jarasiunas, Kestutis, et al., "Nonresonant Four-Wave Mixing in Photorefractive CdTe Crystals Using a Picosecond Parametric Generator", Review of Scientific Instruments, vol. 69, No. 11, pp. 3776-3779, Nov. 1998.

Kamshilin, Alexei, A., et al., "Adaptive Interferometer Using Self-Induced Electro-Optic Modulation", Applied Physics Letters, vol. 77, No. 25, pp. 4098-4100, Dec. 18, 2000.

Kamshilin, Alexei, A., et al., "Linear Sensing of Speckle-Pattern Displacements Using a Photorefractive GaP Crystal", Applied Physics Letters, vol. 74, No. 18, pp. 2575-2577, May 3, 1999.

Kamshilin, Alexei, A., et al., "Polarization Self-Modulation of the Nonstationary Speckle Field in a Photorefractive Crystal", Optics Letters, vol. 24, No. 12, pp. 832-834, Jun. 15, 1999.

Kobozev, Oleg, et al., "Fast Adaptive Interferometer in a GaP Crystal Using a Near-Infrared Laser Diode", Journal of Optics A: Pure and Applied Optics, vol. 3, pp. L9-L11, 2001.

Kuroda, K. et al., "Photorefractive Effect in GaP", Optics Letters, vol. 15, No. 21, pp. 1197-1199, Nov. 1, 1990.

Peng, Leilei, et al., "Adaptive Optical Coherence-Domain Reflectometry Using Photorefractive Quantum Wells", J. Opt. Soc. Am. B, vol. 21, No. 11, pp. 1953-1963, Nov. 2004.

Raita, Erik, et al., "Fast Photorefractive Response in B12SiO20 in the Near Infrared", Optics Letters, vol. 25, No. 17, pp. 1261-1263, Sep. 1, 2000.

Shcherbin, K. et al., "Photorefractive Recording in AC-Biased Cadmium Telluride", Journal of Alloys and Compounds, Elsevier, vol. 371, pp. 191-194, 2004.

Von Bardeleben, H.J., et al., "Defects in Photorefractive CdTe:V: An Electron Paramagnetic Resonance Study", Applied Physics Letters, vol. 63, No. 8, pp. 1140-1142, Aug. 23, 1993.

Ziari, Mehrdad, et al., "Enhancement of the Photorefractive Gain at 1.3-1.5 um in CdTe Using Alternating Electric Fields", J. Opt. Soc. Am. B, vol. 9, No. 8, pp. 1461-1466, Aug. 1992.

Dukhin, A.S., et al., "Use of Ultrasound for Characterizing Dairy Products", J. Dairy Sci., vol. 88, No. 4, pp. 1320-1334, Apr. 2005 (16 pages).

Raita, Erik, Kamshilin, Alexei, A., et al., "Fast Mutually Pumped Phase Conjugation Induced by a Transient Photorefractive Surface Wave", J. Opt. Soc. Am. B, vol. 15, No. 7, pp. 2023-2031, Jul. 1998 (9 pages).

* cited by examiner

FIG. 8 (OPTICAL SUBSYSTEM)

ATTENUATION VS. FREQUENCY FOR FAT DROPS IN WATER

METHOD AND APPARATUS OF DETECTING AN OBJECT

CROSS-REFERENCE TO RELATED APPLICATION

This application claims priority from U.S. Provisional Patent Application Ser. No. 60/677,751, filed on May 4, 2005, the entirety of which is expressly incorporated by reference herein.

STATEMENT AS TO RIGHTS TO INVENTIONS MADE UNDER FEDERALLY-SPONSORED RESEARCH AND DEVELOPMENT

The U.S. Government has provided funding for the background research for this invention through an award by the Department of Defense.

BACKGROUND

1. Field of the Invention

The present invention relates in general to the field of safety, security, and process control. More particularly, the present invention relates to a method and apparatus for detecting potentially harmful objects in a closed container, measuring critical-to-quality parameters in a container's contents for process control, and identifying defects in the container itself.

2. Discussion of the Related Art

As is known to those skilled in the art, the detection of potentially harmful materials in a closed container continues to be a problem. This is particularly true where x-ray radiation cannot be employed for safety or health reasons, lack of sensitivity, or specificity. Other techniques such as contact-based ultrasound, optical spectroscopy, gas chromatography, mass spectroscopy, bio-assay, etc. also lack the ability to perform stand-off, non-invasive, continuous, real-time, non-consumable inspection of closed containers that include plastic, glass, ferrous and non-ferrous metals.

Listed below are various publications that are referenced throughout this application by the convention, author [reference number].

1. ATHERTON, KATHRYN, et al., "Generation and Detection of Broadband Laser Generated Ultrasound From Low Power Laser Sources", Photonics 2000: International Conference on Fiber Optics and Photonics, Proceedings of SPIE, vol. 4417, pgs. 19-32, 2001.
2. BLOUIN, ALAIN, et al., "Detection of Ultrasonic Motion of a Scattering Surface by Two-Wave Mixing in a Photorefractive GaAs Crystal", Applied Physics Letters, vol. 65, no. 8, pgs. 932-934, Aug. 22, 1994.
3. CAMPAGNE, BENJAMIN, et al., "Compact and Fast Response Ultrasonic Detection Device Based on Two-Wave Mixing in a Gallium Arsenide Photorefractive Crystal", Review of Scientific Instruments, vol. 72, no. 5, pgs. 2478-2482, May 2001.
4. DELAYE, PHILIPPE, "Heterodyne Detection of Ultrasound From Rough Surfaces Using a Double Phase Conjugate Mirror", Applied Physics Letters, vol. 67, no. 22, pgs. 3251-3253, Nov. 27, 1995.
5. DELAYE, PHILIPPE, et al., "Detection of Ultrasonic Motion of Scattering Surface by Photorefractive InP:Fe Under an Applied dc Field", J. Opt. Soc. Am. B, vol. 14, no. 7, pgs. 1723-1734, July 1997.
6. GLASS, A. M., et al., "Four-Wave Mixing in Semi-Insulating InP and GaAs Using the Photorefractive Effect", Applied Physics Letters, vol. 44, no. 10, pgs. 948-950, May 15, 1984.
7. GOLOVAN, L. A., et al., "Efficient Nonlinear Optical Conversion in Porous GaP—The Effect of Light Localization", Photonic Crystal Materials and Devices II, Proceeding of SPIE, vol. 5360, pgs. 333-338, 2004.
8. HONDA, TOKUYUKI, et al., "Optical Measurement of Ultrasonic Nanometer Motion of Rough Surface by Two-Wave Mixing in Bi12SiO20", Jpn. J. Appl. Phys., vol. 34, part 1, no. 7A, pgs. 3737-3740, July 1995.
9. IIDA, YASUHIRO, et al., "Detection of Small In-Plane Vibrations Using the Polarization Self-Modulation Effect in GaP", Journal of Optics A: Pure and Applied Optics, vol. 5, pgs. S457-S461, 2003.
10. ING, R. K, et al., "Broadband Optical Detection of Ultrasound by Two-Wave Mixing in a Photorefractive Crystal", Applied Physics Letters, vol. 59, no. 25, pgs. 3233-3235, Dec. 16, 1991.
11. ING, R. K., et al., "Ultrasound Detection on Rough Surfaces Using Heterodyne Photorefractive Interferometer: Applications to NDE", IEEE Ultrasonic Symposium, pgs. 681-684, 1996.
12. JARASIUNAS, KESTUTIS, et al., "Nonresonant Four-Wave Mixing in Photorefractive CdTe Crystals Using a Picosecond Parametric Generator", Review of Scientific Instruments, vol. 69, no. 11, pgs. 3776-3779, November 1998.
13. KAMSHILIN, ALEXEI, A., et al., "Adaptive Interferometer Using Self-Induced Electro-Optic Modulation", Applied Physics Letters, vol. 77, no. 25, pgs. 4098-4100, Dec. 18, 2000.
14. KAMSHILIN, ALEXEI, A., et al., "Linear Sensing of Speckle-Pattern Displacements Using a Photorefractive GaP Crystal", Applied Physics Letters, vol. 74, no. 18, pgs. 2575-2577, May 3, 1999.
15. KAMSHILIN, ALEXEI, A., et al., "Polarization Self-Modulation of the Nonstationary Speckle Field in A Photorefractive Crystal", Optics Letters, vol. 24, no. 12, pgs. 832-834, Jun. 15, 1999.
16. KOBOZEV, OLEG, et al., "Fast Adaptive Interferometer in a GaP Crystal Using a Near-Infrared Laser Diode", Journal of Optics A: Pure and Applied Optics, vol. 3, pgs. L9-L11, 2001.
17. KURODA, K. et al., "Photorefractive Effect in GaP", Optics Letters, vol. 15, no. 21, pgs. 1197-1199, Nov. 1, 1990.
18. PENG, LEILEI, et al., "Adaptive Optical Coherence-Domain Reflectometry Using Photorefractive Quantum Wells", J. Opt. Soc. Am. B, vol. 21, no. 11, pgs. 1953-1963, November 2004.
19. RAITA, ERIK, et al., "Fast Photorefractive Response in Bl2SiO20 in the Near Infrared", Optics Letters, vol. 25, no. 17, pgs. 1261-1263, Sep. 1, 2000.
20. SCRUBY, C. B., et al., Laser Ultrasonics: Techniques and Applications, Adam Hilger, Bristol, England, 1990.
21. SHCHERBIN, K. et al., "Photorefractive Recording in AC-Biased Cadmium Telluride", Journal of Alloys and Compounds, Elsevier, vol. 371, pgs. 191-194, 2004.
22. SMULKO, et al., Sensors and Materials Volume 16, in press, 2004.
23. STEPANOV, S., et al., Photorefractive Materials and Their Applications: Fundamental Phenomena, ed. P. Gunter, et al., Springer, Berlin, pg. 263.
24. VON BARDELEBEN, H. J., et al., "Defects in Photorefractive CdTe:V: An Electron Paramagnetic Resonance Study", Applied Physics Letters, vol. 63, no. 8, pgs. 1140-1142, Aug. 23, 1993.

25. ZIARI, MEHRDAD, et al., "Enhancement of the Photo-refractive Gain at 1.3-1.5 μm in CdTe Using Alternating Electric Fields", J. Opt. Soc. Am. B, vol. 9, no. 8, pgs. 1461-1466, August 1992.

The disclosures of all these publications in their entirety are hereby expressly incorporated by reference into the present application for at least the purposes of indicating the background of the present invention and illustrating the state of the art. Various authors have reported schemes for interferometers. For example, Kamshilin et al. introduced an interferometric technique for linear detection of small ultrasonic out-of-plane vibrations of a rough surface. This technique is based on the polarization self-modulation (PSM) effect in photorefractive crystals under an applied AC field that excludes the field screening. The performance of the PSM interferometer was experimentally demonstrated in photorefractive sillenite crystals ($B_{i12}Ti_{O20}$) by Kamshilin et al., and in photorefractive GaP crystals by Kobozev et al. [16].

The disclosures of all the below-referenced prior United States patents are hereby expressly incorporated by reference into this present application for purposes including, but not limited to, indicating the background of the present invention and illustrating the state of the art: U.S. Pat. No. 4,455,268 discloses a "Control System for Processing Composite Materials", U.S. Pat. No. 4,758,803 discloses a "Marginal Oscillator for Acoustic Monitoring of Curing of Plastics", U.S. Pat. No. 4,862,384 discloses a "Method of Using Dynamic Viscosity Using Acoustic Transducer", U.S. Pat. No. 5,505,090 discloses a "Method and Apparatus for Non-Destructive Inspection of Composite Materials and Semi-Monocoque Structures", U.S. Pat. No. 5,533,399 discloses a "Method and Apparatus for Non-Destructive Measurement of Elastic Properties of Structural Materials", and U.S. Pat. No. 6,029,520 discloses an "Ultrasonic Monitoring of Resin in a Press for the Production of Particle Board and Similar Materials."

However, what is needed is a cost-effective, accurate way to make measurements of things (e.g., containers, fluid-filled containers, etc.), and fulfill one or more of the following inspection conditions: portable, stand-off, non-invasive, continuous, real-time, non-radiological, and non-consumable.

SUMMARY

By way of summary, embodiments of the present invention are directed to an inspection system with a sensor. This system has the capability for stand-off, non-invasive, continuous, real-time, non-radiological, non-consumable, eye-safe inspection of closed containers (e.g., shipping containers, drums, or tanks used for transporting liquids) made of a wide variety of materials that include ferrous metals, non-ferrous metals, glass, plastics, and organic material.

According to one embodiment of the invention, the system or apparatus comprises at least one pulsed laser emitter for directing energy at the surface of an object, wherein the ultrasonic wave is generated within the object to be characterized, and a remote means of measuring the vibrational excitation in the object, whereby the object is remotely characterized. The remote means of measuring the vibrational excitation can include a laser vibrometer. The object to be characterized can include a mold containing powders, liquids or solids.

In another embodiment, the invention provides a remote sensing device for determining the attributes of a container. The remote sensing device comprises a means for determining at least one of container dimensions, container materials, and container defects; a means for detecting at least one of a solid, a liquid, a gas, and mixtures of a solid, a liquid, and a gas; a means for detecting at least one of chemicals flowing in a pipe, waste flowing in a stream or river, and pollutants in a liquid stationary in a pool or tank; and a means for sampling by at least one mechanical/acoustical vibration, infrasonic means, audible means, and ultrasonic means. The means for sampling may have a vibration launched by electromagnetic radiation, radio/microwave radiation, or terahertz radiation. The device may include an optical sensor, which can sense at least one of infrared, visible light, and ultraviolet. In addition, the device may include a pulsed laser with a generator for generating at least one of a single pulse, multiple pulses, a uniform time interval, a varying time interval, a pulse compression, a shaped pulse, and a phased array. The device may also include an X-ray generator and detector, as well as an interferometer vibrometer. The device may further include two-wave mixing or four-wave mixing.

Stand-off means that the sensor preferably operates in close proximity (millimeters) or at a long distance (kilometers) with certain adjustments to the basic design. According to embodiments of the invention, the sensor preferably uses laser-based ultrasound generation and detection which has been shown to be a viable stand-off detection technology.

Non-invasive means that the sensor preferably determines material properties of the contents of a container closed to material flow. According to embodiments of the invention, the sensor preferably uses laser-based ultrasound generation and detection, which has been shown to be a viable non-invasive detection technology.

Continuous means that the sensor preferably takes many consecutive measurements without intervention. According to embodiments of the invention, the sensor has a repetition rate between 1 and 10 Hz and can collect data continually from the sample as long as the sensor is aimed at the container.

Real-time means that the results preferably are available within seconds or fractions of seconds. According to embodiments of the invention, the sensor preferably has a repetition rate between 1 and 10 Hz and can collect data continually from the sample as long as the sensor is aimed at the container.

Non-radiological means that the sensor preferably does not require the use of materials that undergo radioactive decay to produce an energy source for the sensor. According to embodiments of the invention, the sensor preferably uses laser radiation at 1.5 μm, which is considered by the literature as the "eye-safe" region of the electromagnetic spectrum.

Non-consumable means that the sensor preferably does not require chemical or biological ingredients that are consumed by the activity of sensing. According to embodiments of the invention, the entire sensor preferably consists of hardware and software, as described in the parts lists and associated figures, that does not require use of any disposable test kits, ingredients, or other consumable media.

Eye-safe means that the sensor preferably does not emit radiation that is destructive to the human eye. According to embodiments of the invention, the sensor preferably uses laser radiation at 1.5 μm, which is considered by the literature as the "eye-safe" region of the electromagnetic spectrum.

Another aspect of the invention is to provide an apparatus that is ruggedized and reliable, thereby decreasing down time and operating costs.

Still another aspect of the invention is to provide an apparatus that has one or more of the characteristics discussed above, but which is relatively simple to manufacture, assemble, and use using a minimum of equipment, time, and resources. In one such manufacturing process, subsystems would be purchased from other manufacturers, and final assembly and integration of these subsystems would be done at a central location.

Another aspect of the invention is to provide a non-invasive process sensor to monitor the phase transition of the cross linking process that occurs in manufacture of polymer products.

Yet another aspect of the invention is to perform a stand-off, non-invasive inspection of returnable beverage kegs for frozen beverages or non-nominal material contents.

Still another aspect of the invention is to perform stand-off, non-invasive level inspection of beverage cans and bottles without the use of radiological materials.

Yet another aspect of the invention is to perform stand-off, non-invasive inspection of drums, tanks, pipes (e.g., fluid-filled pipes), warheads, bombs, and other closed containers for chemical and/or biological weapons. Closed containers for chemical and/or biological weapons are generally made of either ferrous, non-ferrous, polymer, or glass containers.

Another aspect of the invention is to detect defects during the creation of laminate materials.

Still another aspect of the invention is to detect contraband in tires of vehicles moving through border inspection stations. Another aspect of the invention is to verify contents in containers shipped across US borders. Still another aspect of the invention is to identify flow characteristics in pipelines, which is currently being done using contact-based ultrasound sensors (e.g., by General Electric). Another aspect of the invention is to identify defects in pipelines.

Yet another aspect of the invention is to provide quality assurance of canned and bottled food products using a continuous, real-time, noninvasive sensor. Another aspect of the invention is to detect a small amount of biological material, for example, a few drops of biological material (dairy fat, blood), in a closed container of water.

Still another aspect of the invention is to measure mixtures of materials inside a closed container. Another aspect of the invention is to provide a method that can be used to satisfy the above aspects of the invention. Still another aspect of the invention is to provide a method that is predictable and reproducible, thereby decreasing variance and operating costs.

Another aspect of the invention is to provide a method that has one or more of the characteristics discussed above, but which is relatively simple to set up and operate using relatively low-skilled workers.

These and other aspects and objects of the present invention will be better appreciated and understood when considered in conjunction with the following description and the accompanying drawings. It should be understood, however, that the following description, while indicating preferred embodiments of the present invention, is given by way of illustration and not of limitation. Many changes and modifications may be made within the scope of the present invention without departing from the spirit thereof, and the invention includes all such modifications.

DETAILED DESCRIPTION

The present invention and the various features and advantageous details thereof are explained more fully with reference to the non-limiting embodiments described in detail in the following description.

1. System Overview

In one embodiment, the inventive system of the present invention includes an optical device that may be mounted on an optical "breadboard." The breadboard may be mounted on a rail to enable the distance between a sensor of the system and a target container to be varied in a controllable way.

Figure 6:
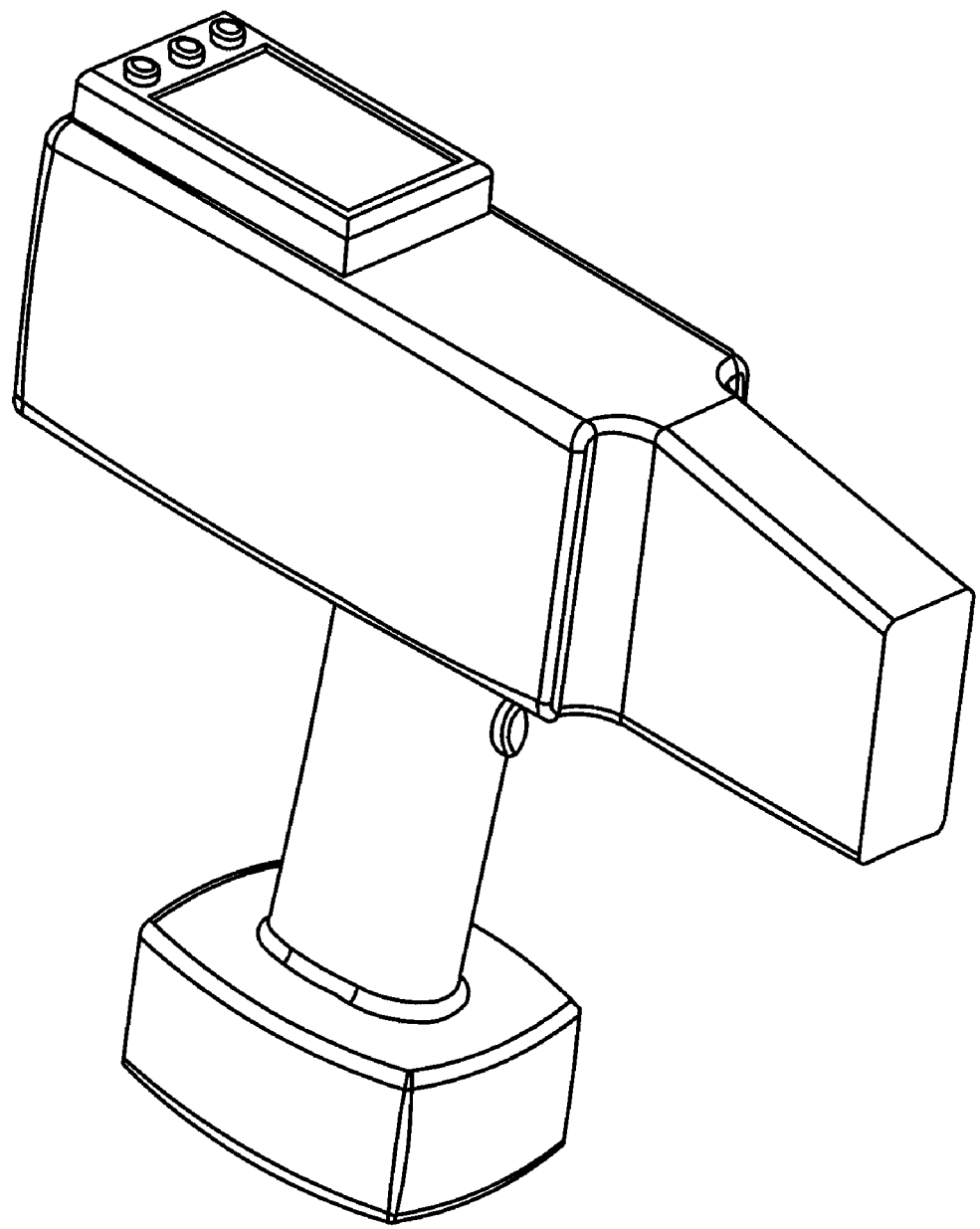
FIG. 6 shows one embodiment of a hand-held, mobile package according to an embodiment of the present invention.

In another embodiment, the inventive system of the present invention includes all optics, electronics, and software in a single hand-held unit, such as, for example, shown in FIG. 6.

The preferred optical device includes an excitation laser that will be a Q-switched Nd:YAG laser pumped with a laser diode. The entire laser will be preferably housed in a TO-3 case; and have a wavelength of 1.550 μm, pulse energy of 100 μA pulse width of 2 ns, peak power of 50 kW, and repetition rate of SS-10 Hz. The supplied driver is designed to work from a 3V battery. The excitation beam is preferably launched through an optional pattern generator and is directed collinear with probe and detection beams to minimize angle and distance-dependent focusing effects. A filter is preferably inserted to prevent excitation beam energy from reaching the detector. The high impulse energy and low continuous power make this embodiment ideal for mobile applications.

A probe laser preferably consists of a CW laser diode (1550 nm, 130 mW). The probe laser beam preferably is launched through an optional pattern generator into a beam splitter. The beam splitter directs a first part of the beam towards the target (probe or transmitted material wave beam) and a second part of the beam towards a photorefractive crystal of CdTe or similar (reference beam). Two-wave mixing takes place in the photorefractive crystal, and the resulting signal is detected by a high-speed differential detector consisting of a polarizing beam splitter and two photodiodes.

As mentioned, in one embodiment a high peak power Q-switched solid-state laser is used for the excitation source. However, this traditional approach involves high-energy optical pulse irradiation that may lead to surface damage, especially in carbon or glass fiber composites. Therefore, in another embodiment, the simple projection system is substituted with a pattern-based projection system. This enables excitation without damage but requires coded temporal signals. Arrays of patterns generated by semiconductor laser sources may also produce very broadband acoustic signals, both temporally and spatially.

In one preferred embodiment, the probe laser is a low-cost near-infrared laser diode (1550 nm, 130 mW). The optical arrangement may also have a provision for holographic pattern generation to allow for decoding of encoded excitation laser signals.

The use of laser diodes in the region of 1550 nm allows the entire system to be eye-safe. The system could be created at other wavelengths of light using optical components appropriate for the selected wavelength of light. Of course, the system could be replaced by other radiation sources such as microwaves.

Semiconductor crystals are known to possess a high mobility of charge carriers, resulting in fast formation of the space-charge field. Others including Delaye [4], Ing et al. [11], Campagne et al. [3], Iida et al. [9], Blouin et al. [2], Golovan et al. [7], Kobozev et al. [16], and Kuroda et al. [17] have also demonstrated photorefractive-based interferometers based on semiconductor crystals. The GaP crystal is representative of a wide-band gap semiconductor, and exhibits the photorefractive effect in red and near-infrared regions of the optical spectrum. In particular, two-wave mixing at red light (wavelength of 633 nm) was first observed in the GaP crystal by Kuroda et al. [17]. It was shown that the response time of the space-charge-field formation in the GaP crystal is about 5 ms at a light intensity of 100 mW cm$^2$. Linear sensing of speckle-pattern displacements using the PSM effect was demonstrated in a GaP crystal at the same wavelength. For practical implementation, the material has to show some potential in the near-infrared region because of the availability of low-cost laser diodes in this spectral region. This has been demonstrated by Kobozev et al. [16], who has reported observations of the fast response time of space-charge-field formation obtained in the photorefractive GaP crystal in the near-infrared region (wavelength of 807 nm). By using the PSM interferometer for the detection of small out-of-plane vibrations, Kobozev et al. [16] found that a response time of a few milliseconds can be achieved with commercially available laser diodes.

Kobozev et al. [16] carried out experiments with a GaP crystal cut in the form of a parallelepiped with edges parallel to the [1$\overline{1}$0], [001] and [110] crystallographic axes. The dimensions of the sample were 3.97, 5.8 and 6.52 mm, respectively. To apply external voltage, silver electrodes were evaporated on the (110) faces of the crystal. The light beams propagated at small angles to the [110] crystallographic axis. The semi-insulating GaP single crystal (point symmetry group $\overline{4}$3m) was grown at Sumitomo Metal Mining Co., Japan.

Kobozev et al. [16] pointed out that the above-described laser diode had a complicated beam intensity profile, which was far from a Gaussian distribution. Nevertheless, this did not limit the performance of the PSM interferometer. Despite large losses of the scattered light, the high intensity of the reference beam provides a fast response.

Shcherbin et al. [21] and others (Von Bardeleben et al. [24], Jarasiunas et al. [12]) have shown a CdTe crystal, which exhibits the largest electro-optic constant among all known semiconductors, to be suitable for photorefractive applications in the near-infrared region.

The data-acquisition system of the present invention preferably includes a signal processor. The stimulus and response signals are managed with a combination of analog and digital strategies. The focus is in digital technologies, which may be reconfigured for different applications.

Amplification is preferably performed with an off-the-shelf pulser/receiver that has noise referred to the input of about 100 μV (pk-pk). This is within the dynamic range of 16-bit A/D converters (65536 counts from 0 to 5 Vdc gives a resolution of 76 μV). In this case, signal conditioning consists of impedance conversion/matching and band-pass filtering with no gain required. If 12-bit converters are used, then some gain will be required, as 4096 counts from 0 to 5 Vdc gives a resolution of 1.2 mV. As such, it is desirable to have computer control of the gain.

Three factors affecting A/D conversion are sample rate, dynamic range, and memory depth. For sample rate, a "digital radio" is used for maximum gain flexibility. In other words, a sensor is connected directly to an A/D converter. To sample components up to 10 MHz, not less than 20 M samples/second (preferably more) are used. The limiting factor is the anti-aliasing filter provided. Actual bandwidth may end at the knee of the filter skirt when the bottom of the skirt reaches the noise floor at 10 MHz. A 96 dB low pass filter provides a 5 MHz bandwidth.

For dynamic range, off-the-shelf converters may be used having typical binary outputs with either 12- or 16-bit resolution. In some instances, 20- or even 24-bit converters may be used. Preferably, if the signal levels and attenuation characteristics are known, then dynamic range becomes less important. On the other hand, if sample thickness and ultrasound attenuation vary greatly, dynamic range is needed. Further, this is less important if a computer controls preamp gain.

For memory depth, there is a need to accommodate several megabytes of sample depth particularly in the design of a commercial system. An adaptive system that first seeks the return signal and then dynamically windows the process to minimize sample depth is desired.

Digital signal processing (DSP) may be performed in real-time at 20 million samples per second and is processor-sensitive. However, samples may be captured at that rate and then analyzed off-line at a much slower rate. Since the repetition rate may be arbitrarily slow, off-line processing may be accomplished at this slower pace. This avoids the need to have DSP-specific hardware for computation. In one embodiment, data may be captured from the digital oscilloscope and stored to a PC. The system may then apply signal processing algorithms to the data.

2. Detailed Description of Preferred Embodiments

The inventive system according to an embodiment of the invention is generally constructed in accordance with what is shown in FIGS. 1-8. The system may be employed in a variety of environments including airports, military bases, manufacturing sites, transportation centers, construction sites, and border patrol checkpoints. The implementation details of various subcomponents of this invention are well known to those skilled in the art, and therefore a detailed description thereof is not necessary to fully understand the present invention.

Figure 1:
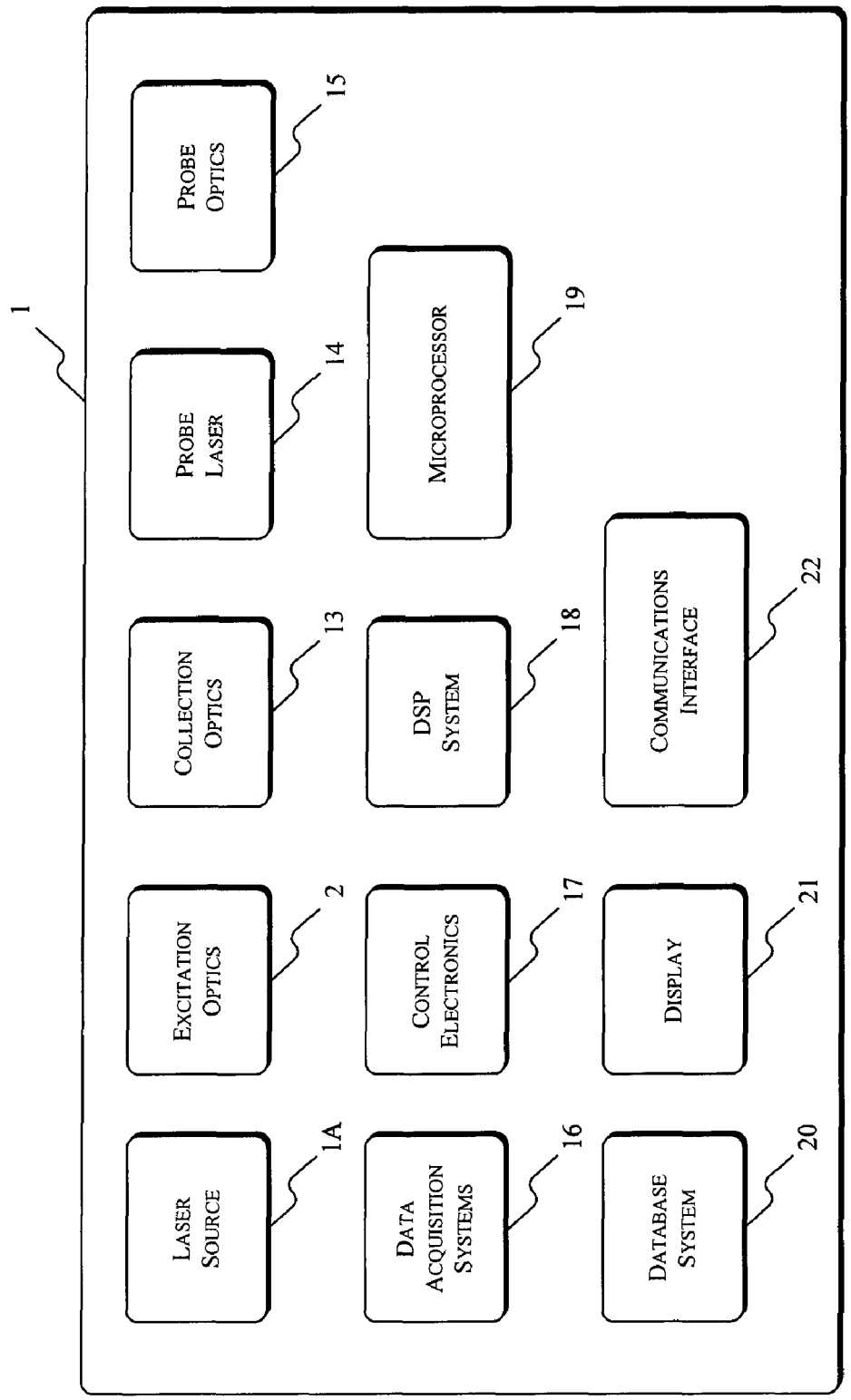
FIG. 1 shows a system according to an embodiment of the invention.

FIG. 1 shows a system 1 according to an embodiment of the invention. The system 1 includes a laser source 1a, excitation optics 2, collection optics 13, a probe laser 14, probe optics 15, data acquisition systems 16, control electronics 17, digital signal processing system 18, a microprocessor 19, and a database system 20. The system 1 also may include a display 21 and a communications interface 22 (e.g., Ethernet, RF, etc.).

Figure 2:
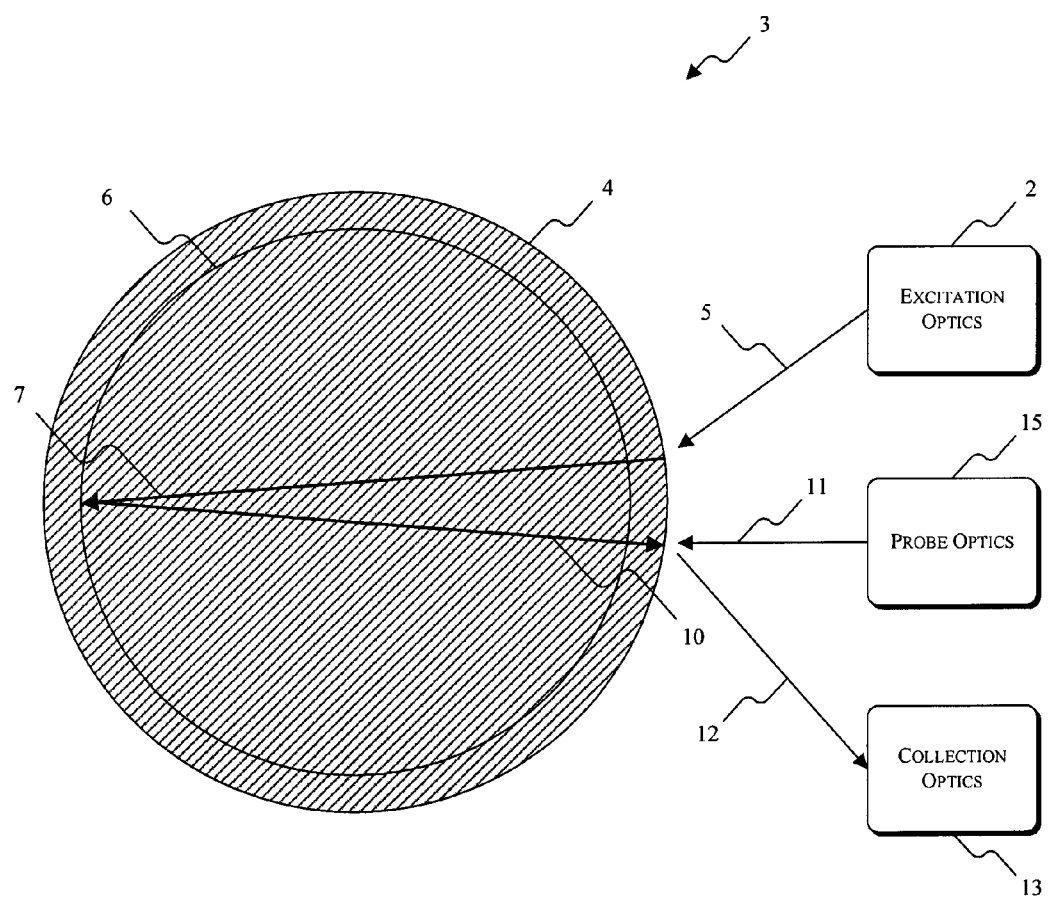
FIG. 2 shows one embodiment of the present invention with a transmitted material wave and reflected material wave probing the material properties of the contents of a container.
Figure 3:
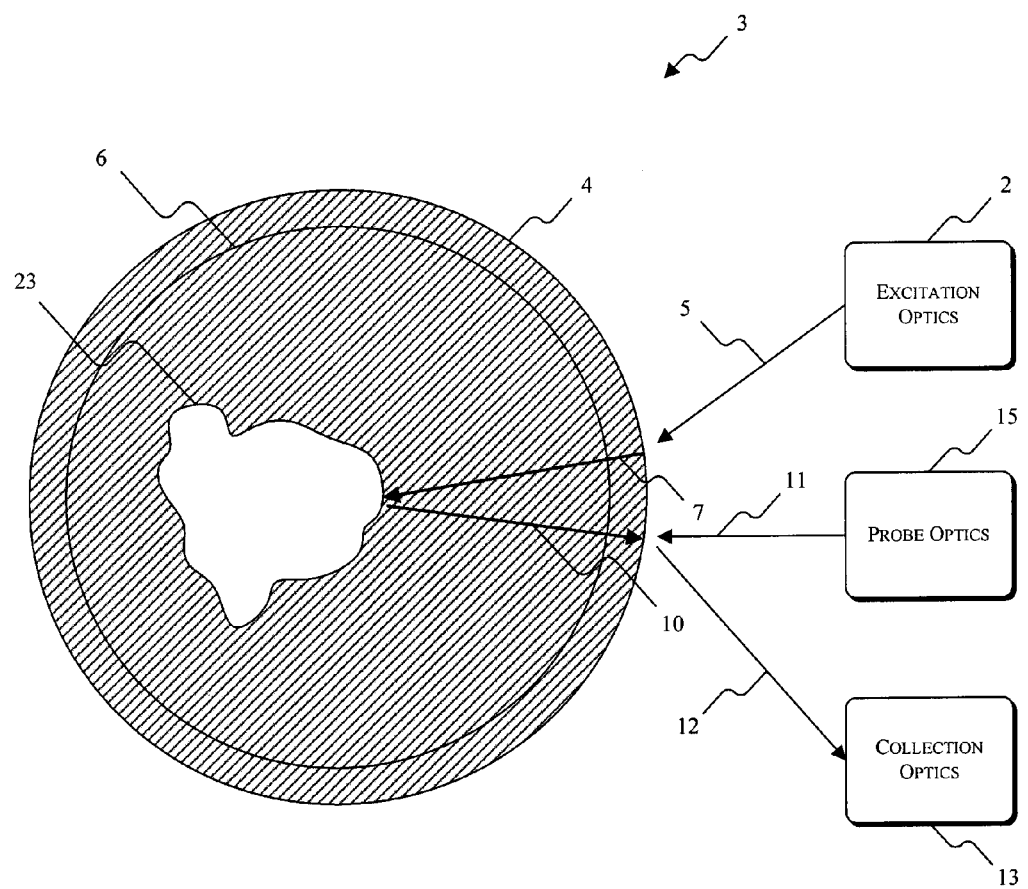
FIG. 3 shows one embodiment of the present invention with a transmitted material wave and reflected material wave probing the material properties of a contaminant of the contents of the container.
Figure 4:
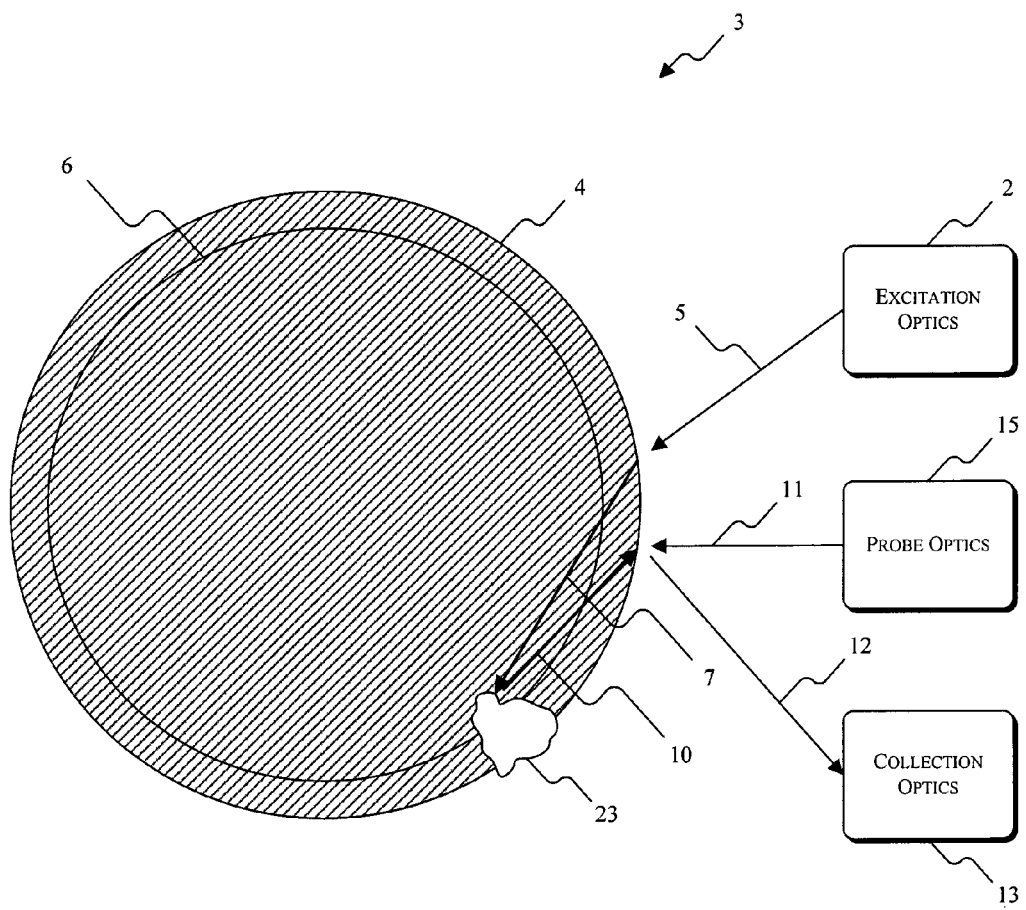
FIG. 4 shows one embodiment of the present invention with a transmitted material wave and reflected material wave probing the material defect in the container.
Figure 5:
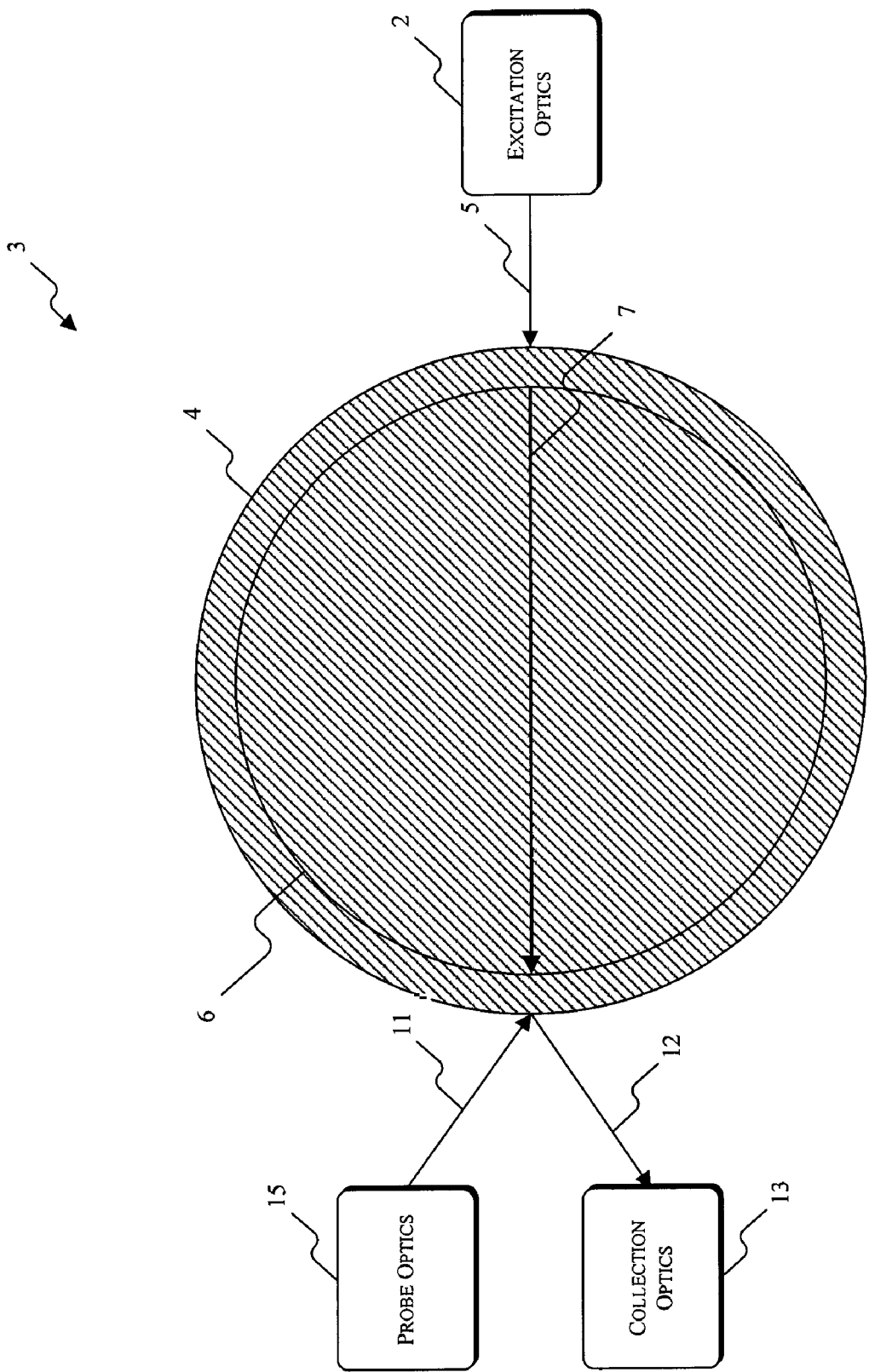
FIG. 5 shows one embodiment of the present invention with a transmitted material wave being detected on the opposite side of the container.

FIGS. 2-5 show the system 1 in use in connection with an exemplary container according to various embodiments of the invention. Specifically, FIG. 2 shows a transmitted material wave and reflected material wave probing the material properties of the contents of a container. FIG. 3 shows a transmitted material wave and reflected material wave probing the material properties of a contaminant of the contents of the container. FIG. 4 shows a transmitted material wave and reflected material wave probing the material defect in the container. FIG. 5 shows a transmitted material wave being detected on the opposite side of the container.

The laser source 1a is connected to excitation optics 2. The system 1 creates various waves which are directed to container vessel 3 and vessel surface 4 and return from the container vessel 3 to the collection optics 13. By way of example, the waves include the incident excitation wave 5, transmitted material wave 7, reflected material wave 10, incident probe wave 11, and reflected probe wave 12. The incident excitation wave 5 is emitted from the laser source 1a and directed by the excitation optics 2. Upon illumination of the container vessel 3, the excitation wave 5 creates a transmitted material wave 7, which is scattered from object of interest 23 and produces reflected material wave 10. The incident probe wave 11 is emitted from the probe laser 14 and directed by the probe optics 15. The incident probe wave 11 is scattered from the surface of the container vessel 3 that is modulated by the reflected material wave 10. The scattered probe wave creates a reflected probe wave 12 that is collected by the collection optics 13. The waves of the laser 1a are primarily directed at the vessel bulk 6 and are used to make a determination of the container contents. Collection optics 13 preferably work in conjunction with probe optics 15. The data acquisition systems 16 collect the information received by the reflected material wave 10. The object of interest 23 is probed by the various waves of the system 1 to determine the content of the container vessel 3.

The graphs of FIGS. 9-14 and tables herein show the results of some of the tests performed using one embodiment of the present invention. As illustrated in FIGS. 9-14, embodiments of the invention use the ultrasound amplitude, the ultrasound frequency, the ultrasound wave velocity, and the bispectral pattern to identify materials inside closed containers (e.g., completely or substantially completely closed containers). Embodiments of the invention can thus determine unknown contents of closed containers by comparing measured metrics with metrics of known materials (e.g., metrics stored in a database).

Figure 9:
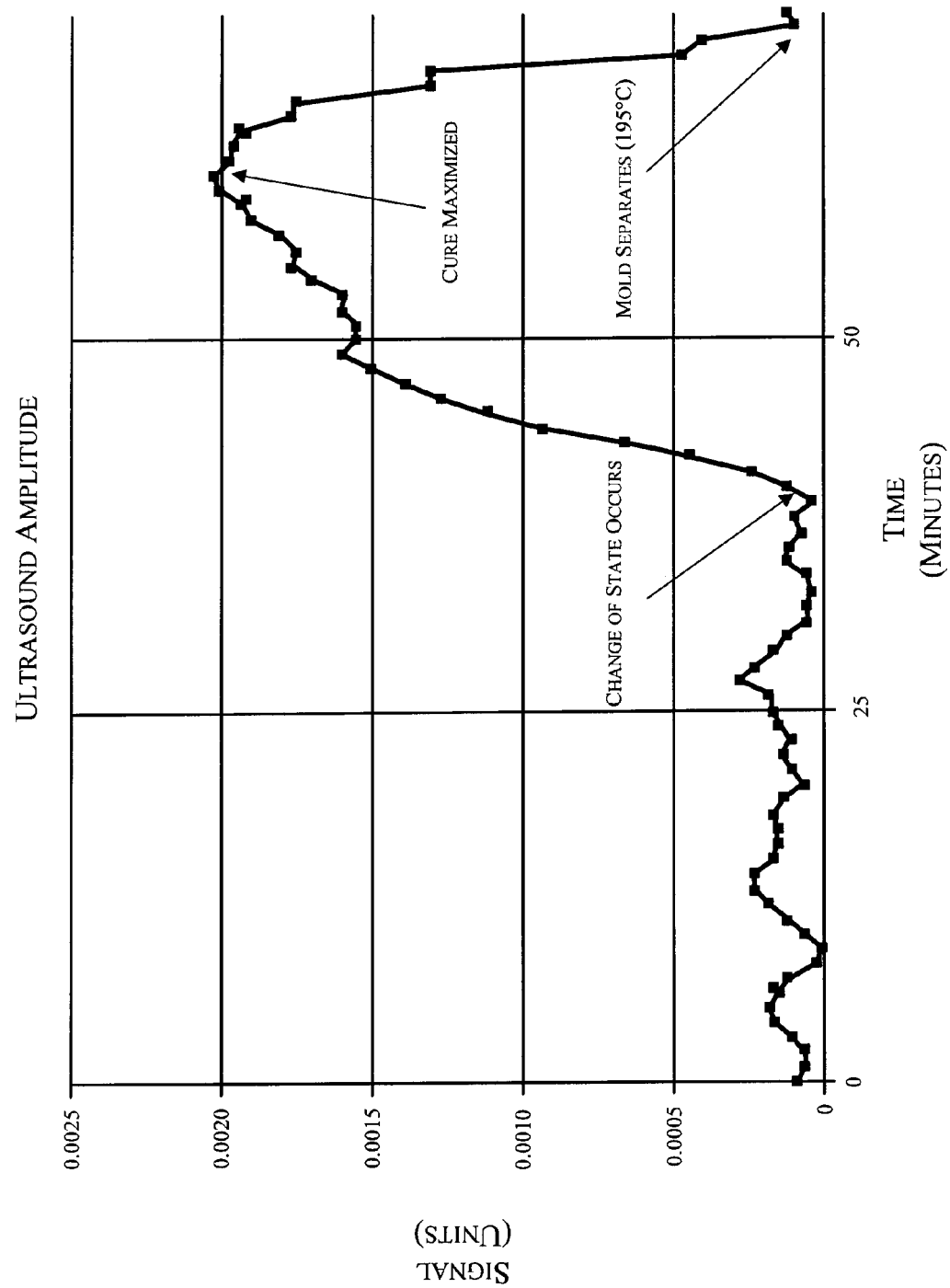
FIG. 9 is a graph that shows measurement of the phase transition in a phenolic friction material manufacture.

FIG. 9 is a graph that shows measurement of the phase transition in a phenolic friction material manufacture. As shown in FIG. 9, in various embodiments of the invention, a sensor system is used to measure the transition from powder, to liquid, and to solid in the manufacture of a composite used for frictional materials.

In FIG. 9, the physical metric measured by the inventive sensor system that indicates the state of the material being processed is the ultrasound amplitude. The ultrasound amplitude is measured using one of the exemplary configurations illustrated in FIGS. 2-5. The graph in FIG. 9 illustrates the following scenario. Powdered material is introduced into the mold. The ultrasound amplitude is low. As the powdered material is heated under pressure, it turns from powder to liquid. When the material becomes liquid, the ultrasound amplitude increases. As time progresses, the material turns from liquid to solid. When the material becomes solid, then the ultrasound amplitude decreases. The solid state of the material indicates that the process is complete.

TABLE 1

| Material | Speed of Sound (mm/µs) |
|---|---|
| Polyethylene | 2.286 |
| Steel | 5.6 |
| SAE 20 Oil | 1.626 |
| Glycerine | 1.753 |
| Water | 1.473 |
| Air | 0.356 |
| Oxygen | 0.33 |

Table 1 shows the speed of sound for various materials (longitudinal mode propagation). The transition time for a wideband ultrasound pulse can easily be measured and along with the physical dimension of the container a speed of sound may be calculated. The speed of sound varies significantly, even in water, as the chemical composition is varied. If the geometry is known then the speed of sound becomes an easy way to differentiate two materials.

Figure 10:
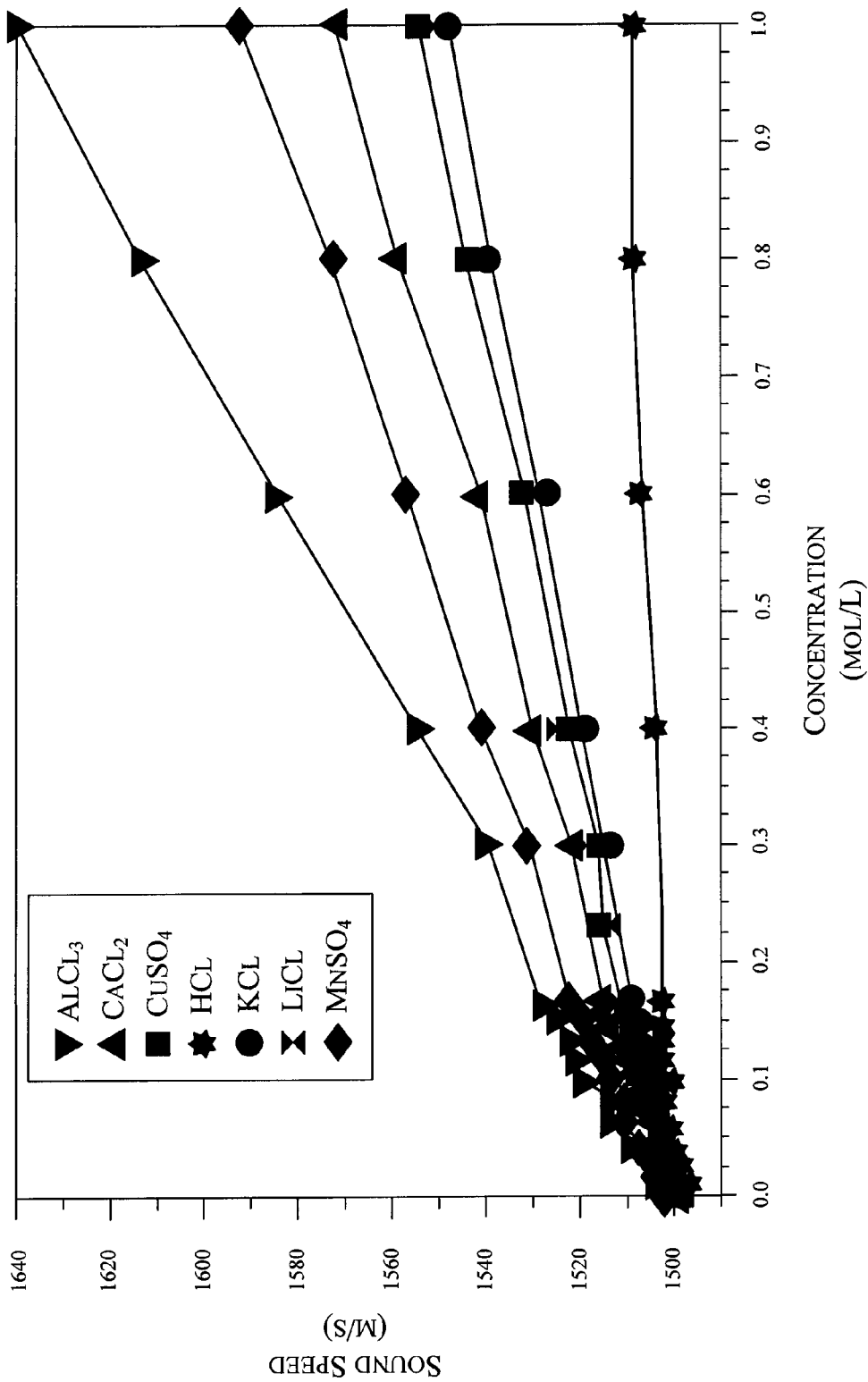
FIG. 10 is a graph that shows sound velocity for differing concentrations of various electrolyte solutions.

FIG. 10 is a graph that shows sound velocity for differing concentrations of various electrolyte solutions (after Dukhin et al.). Embodiments of the invention measure ultrasound velocity using, for example, one of the embodiments of FIGS. 2-5.

Figure 11:
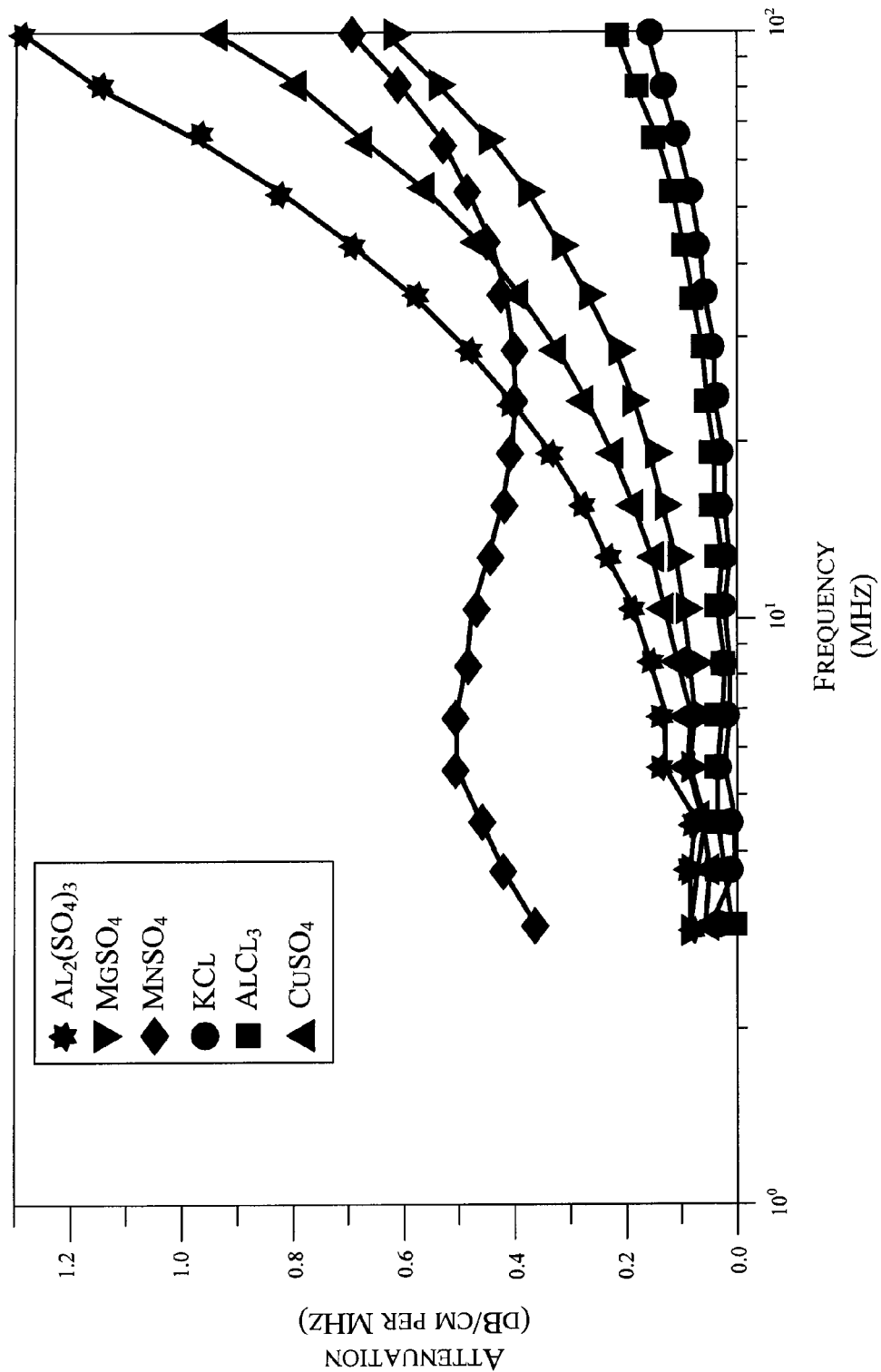
FIG. 11 is a graph that shows frequency dependence of attenuation for various electrolyte solutions.

FIG. 11 is a graph that shows frequency dependence of attenuation for various electrolyte solutions (after Dukhin et al.). Embodiments of the invention are capable of measuring ultrasound velocity using, by way of example, one of the configurations shown in FIGS. 2-5.

Figure 12:
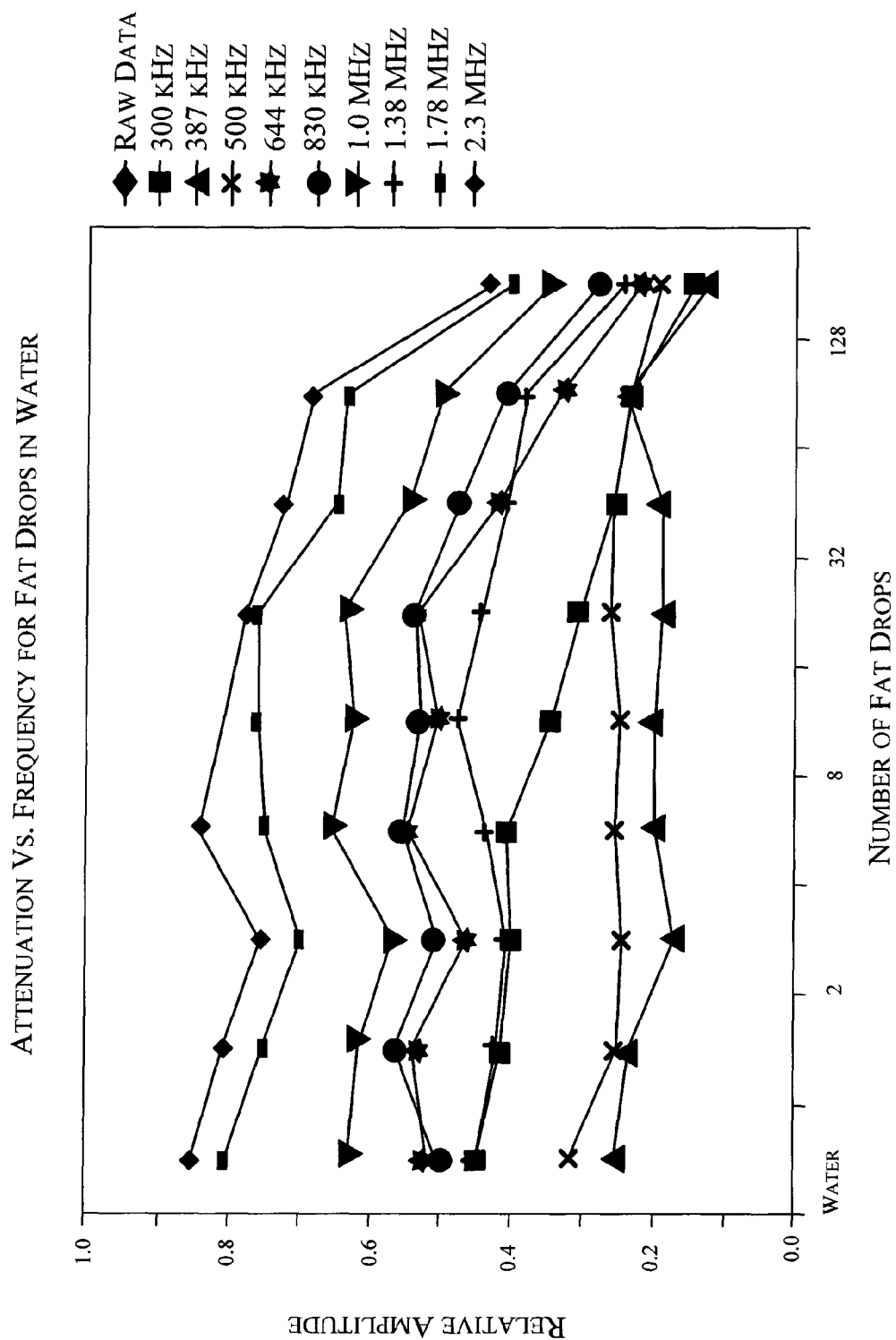
FIG. 12 is a graph that shows amplitude of the measured signal for different frequencies as a function of the number of fat drops added to a container of water.

FIG. 12 is a graph that shows amplitude of the measured signal for different frequencies as a function of the number of fat drops added to a container of water. Embodiments of the invention can detect about a dozen drops of fat in 355 ml of water in an aluminum container. Embodiments of the invention are capable of measuring ultrasound velocity using, for example, one of the configurations shown in FIGS. 2-5.

Figure 13:
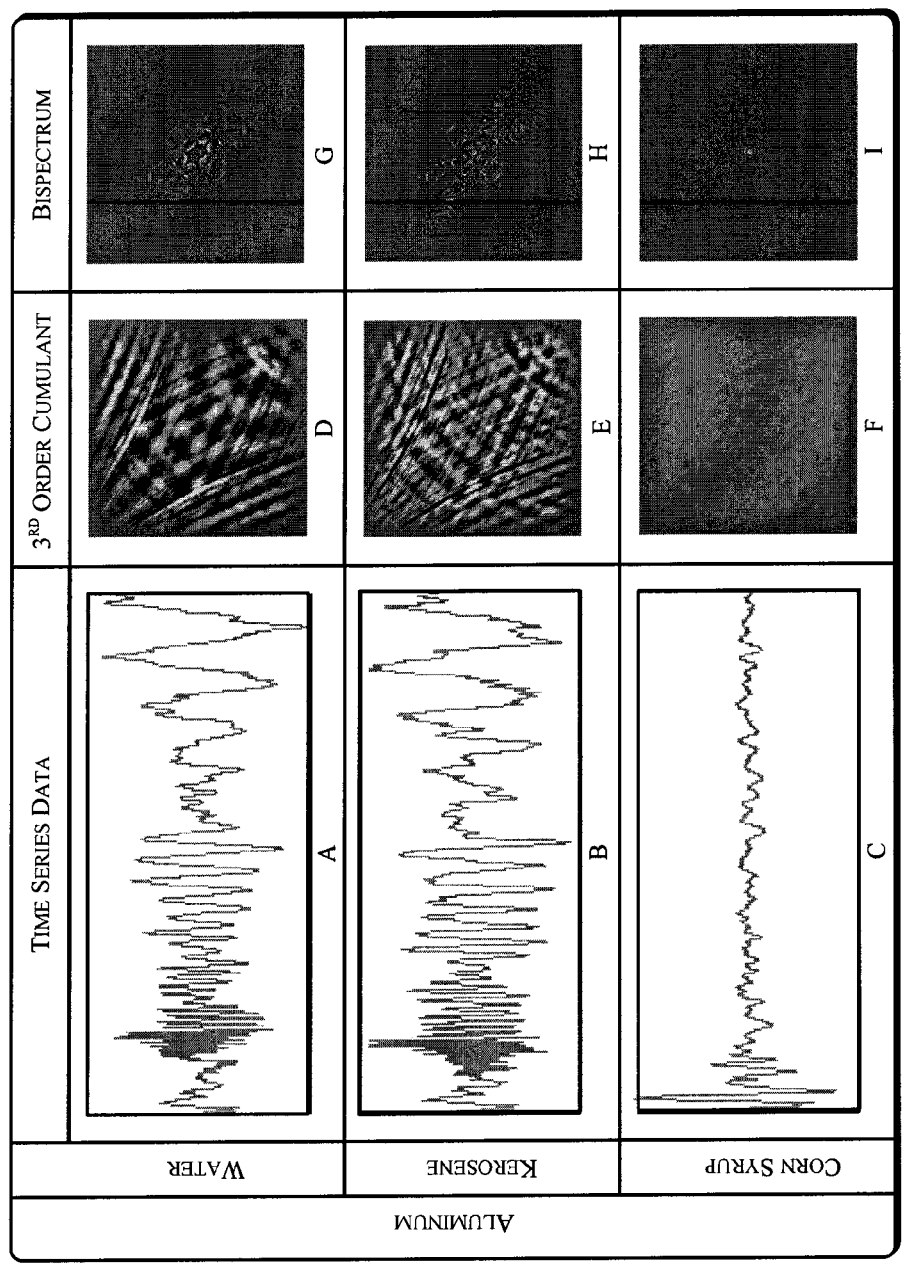
FIG. 13 is a graph that shows a comparison of time series data, $3^{rd}$ order cumulant data, and bispectra data.

FIG. 13 is a graph that shows a comparison of time series data, $3^{rd}$ order cumulant data, and bispectra data. Scale factors are as follows: (Cumulant x-axis and y-axis are both 102.4 µs to +102.4 µs; each pixel is 0.8 µs 256 points) (Bispectra is −312.5 kHz to +312.5 kHz; each point is 4.88 kHz, 128 points) (Time series data is 20 million samples per second, 6500 total samples, 325 µs sample length). FIG. 13 compares data from water, kerosene, and corn syrup in a closed container. FIGS. 13-A, 13-B, and 13-C illustrate representative time series data. The time series data is processed by the microprocessor assembly 83 and the business intelligence subsystem 89 (see FIG. 7) to calculate the 3-D data set described by the $3^{rd}$ order cumulant. The $3^{rd}$ order cumulant for water, kerosene, and corn syrup is illustrated in FIGS. 13-D, 13-E, and 13-F. The $3^{rd}$ order cumulated data is processed by the microprocessor assembly 83 and the business intelligence system 89 to calculate the 3-D data set described by the bispectrum. The bispectrum for water, kerosene, and corn syrup is illustrated in FIGS. 13-G, 13-H, and 13-I. The bispectrum comprises a 3-D data set that displays unique characteristic patterns that are dependent on the original data structure.

Figure 14:
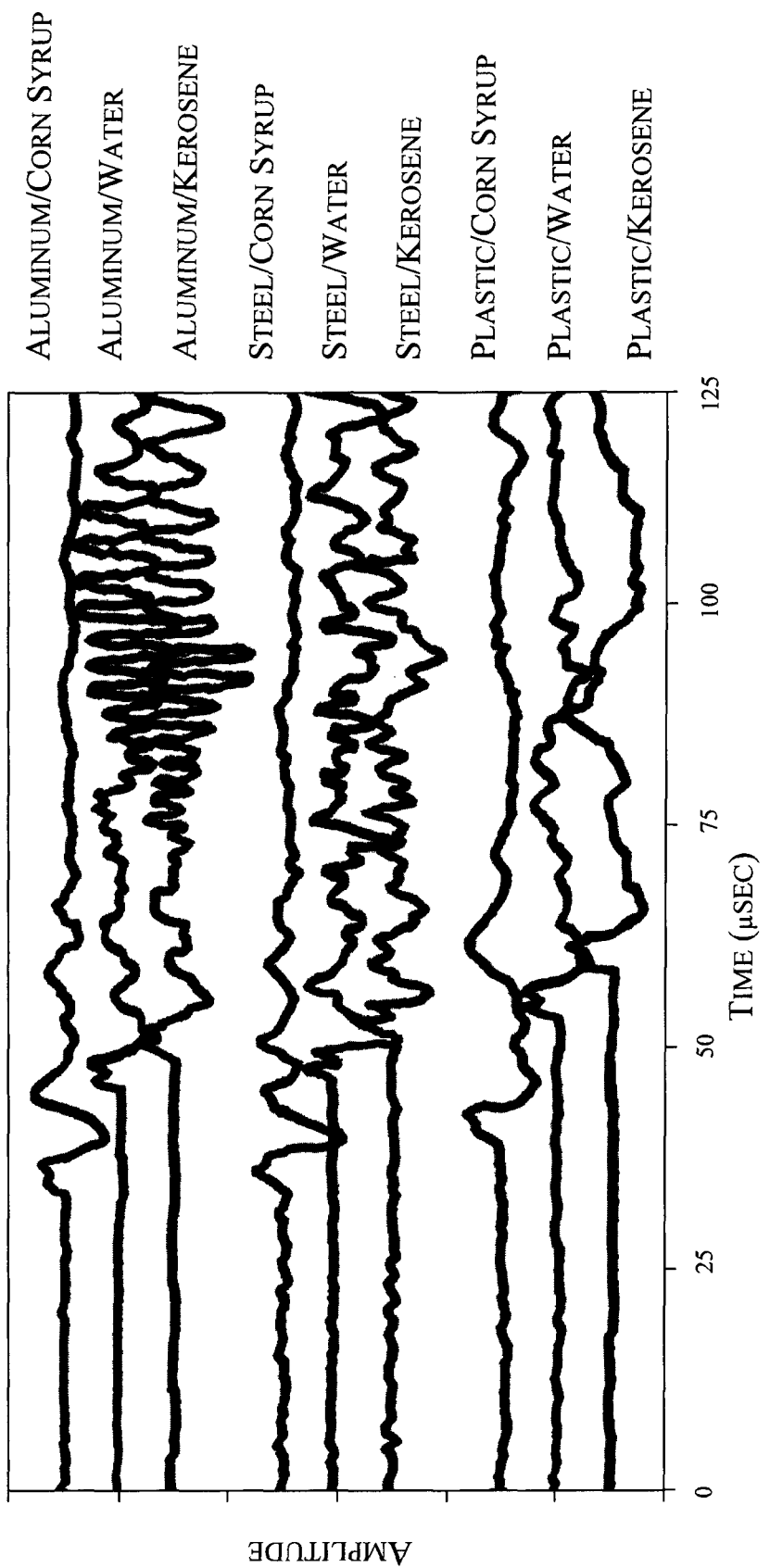
FIG. 14 is a graph that shows time domain ultrasound for nine container/contents combinations.

FIG. 14 is a graph that shows time domain ultrasound for nine container/contents combinations. Three containers made of steel, aluminum, and plastic were filled with corn syrup, kerosene, and water. The speed of sound was measured for each combination in accordance with the embodiments shown in FIGS. 2-5. FIG. 14 and Table 2 illustrate the results of such a measurement and demonstrate the ability of embodiments of the invention to identify corn syrup, kerosene, and water in completely closed containers made from steel, aluminum, or plastic. In particular, Table 2 shows the measured speed of sound using laser-based ultrasound on a number of different containers and contents.

TABLE 2

Measured Speed of Sound Using Laser-Based Ultrasound

| Container | Contents | Time-of-Flight (usec) | Container Diameter (mm) | Measured Speed of Sound (mm/usec.) |
|---|---|---|---|---|
| Steel | Corn Syrup | 35.5 | 66 | 1.859 |
| Aluminum | Corn Syrup | 34.2 | 66 | 1.930 |
| Plastic | Corn Syrup | 39.7 | 75.7 | 1.902 |
| Steel | Kerosene | 52.3 | 66 | 1.262 |
| Aluminum | Kerosene | 49.5 | 66 | 1.333 |
| Plastic | Kerosene | 58.6 | 75.7 | 1.292 |
| Steel | Water | 46.9 | 66 | 1.407 |
| Aluminum | Water | 45.8 | 66 | 1.441 |
| Plastic | Water | 53.7 | 75.7 | 1.410 |

Measured Speed of sound using laser-based ultrasound on a number of different containers and contents.

In one preferred embodiment, analysis of the signals of the system 1 is preferably based on the following:

Timing of the return pulse is used to calculate speed of sound of the material in the container. Spectral analysis is used to determine the frequency and attenuation response of the container and contents. For example, this technique is used to identify various constituents or ingredients in the preparation of food products. VX in the liquid form has a speed of sound similar to water, and the molecular makeup of the material is likely to result in a frequency-dependent spectra that is different than water.

Fluctuation Enhanced Analysis (Kish et al.) is preferably used to investigate the non-Gaussian noise characteristics of the signals that may translate into useful information. Smulko et al. [22] have identified a methodology that suggests that the stochastic component of a chemical sensor signal contains valuable information that can be visualized not only by spectral analysis, but also by methods of higher-order statistics (HOS). The analysis of HOS enables the extraction of non-conventional features that lead to significant improvements in selectivity and sensitivity. In embodiments of the invention, particular attention is paid to the bispectrum that characterizes the non-Gaussian component and detects non-stationary features in analyzed noise. Smulko's results suggest that the bispectrum can be applied for material recognition.

Ultrasound data for each measurement was acquired as multiple time series, which were then phase locked and averaged in software to provide a clear signal, well above the noise floor. The third order cumulant of the processed time series was obtained by the expression:

$$C_{3x}(k, l) = \sum_{n=0}^{n=N} x(n)x(n+k)x(n+l)$$

This was undertaken over the range k=(−128 . . . 128), l=(−128 . . . 128) times a scale factor, with n running over the range (0 . . . 6500), producing the two-dimensional plots shown in FIGS. 13-D, 13-E, and 13-F. A second order Fourier transform was then performed on each cumulant to obtain the bispectrum, by the expression:

$$S_{3x}(f_1, f_2) = \sum_{k=-64}^{64} \sum_{l=-64}^{64} C_{3x}(k, l)e^{-2\pi i f_1 k/256} e^{-2\pi i f_2 l/256}$$

Each bispectrum is plotted in FIGS. 13-G, 13-H, and 13-I in grayscale pixel values, as the sum of the sine and cosine Fourier components.

Figure 7:
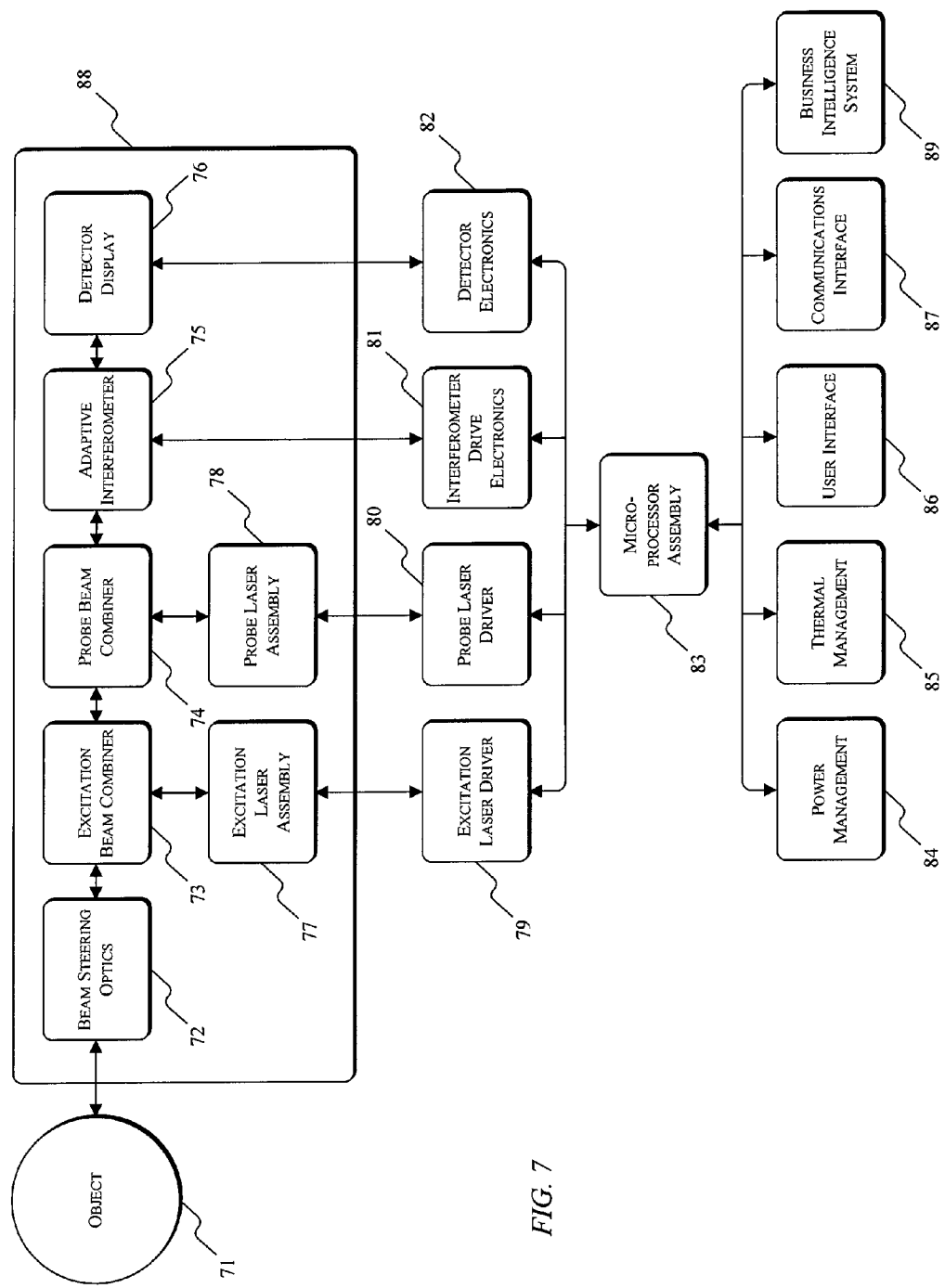
FIG. 7 shows a schematic of one system configuration according to an embodiment of the present invention.

Another example of the preferred embodiment is shown in FIG. 7, which shows an example system configuration. Here, the device under test or object (71) is, for example, a 55 gallon drum or container. The system includes an optical subsystem (88), an excitation beam driver (79), a probe laser driver (80), drive electronics (81), detector electronics (82), a microprocessor assembly (83), a power management subsystem (84), a thermal management subsystem (85), a user interface (86), a communications interface (87), and a business intelligence subsystem (89).

The optical subsystem (88) includes beam steering optics (72), an excitation beam combiner (73), a probe beam combiner (74), an adaptive interferometer (75), a detector assembly (76), an excitation laser assembly (77), and a probe laser assembly (78).

Beam steering optics (72) is, for example, a telephoto lens. The excitation beam combiner (73) is preferably a beam splitter. The probe beam combiner (74) is, for example, a beam splitter. The preferred adaptive interferometer (75) is a photorefractive crystal, mirror, and polarizer. In one embodiment of the invention, the adaptive interferometer (75) includes a single beam interferometer. In another embodiment, the adaptive interferometer (75) includes a reference beam interferometer. The detector assembly (76) is, for example, a beam splitter differential photo-detector combination. The excitation laser assembly (77) includes preferably a Q-switched YAG laser, while the probe laser assembly (78) includes, for example, a diode laser.

The preferred excitation beam driver (79) is a current controller pulsing circuit. The probe laser driver (80) is, for example, a constant current supply with diode feedback. Drive electronics for the adaptive interferometer (81) preferably include a bias supply for a photorefractive crystal. Detector electronics (82), for example, include a differential operational amplifier.

Preferably, the microprocessor assembly (83) is a PC 104 minicomputer module, and power management subsystem (84) includes a power supply battery charging module. Thermal management subsystem (85) includes, for example, a thermoelectric cooler and controller. User interface (86) is, for example, a LCD touch screen module. Communications interface (87) is, for example, a Wi-Fi interface module, Ethernet interface module, USB interface module, or ZigBee interface module. Wi-Fi and ZigBee are known technologies for enabling wireless communication between devices and networks. Business intelligence subsystem (89) is, for example, an application server, database server, application software, and database software and data to provide list parameters for contents of shipping containers and software integration to software manifests of shipping container contents.

Figure 8:
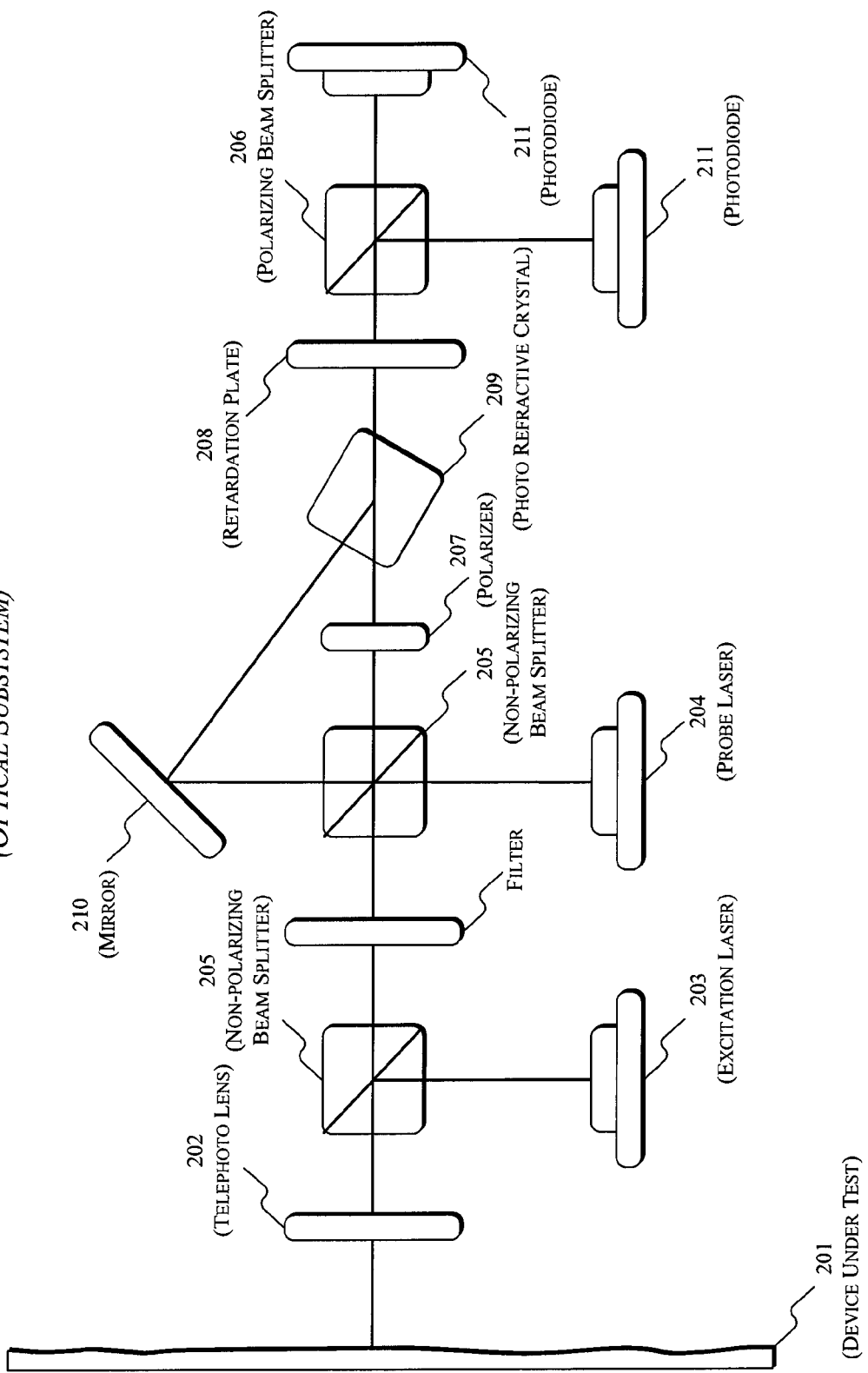
FIG. 8 shows a schematic of one optical subsystem according to an embodiment of the present invention.

Another preferred embodiment of the optical subsystem 88 is shown in FIG. 8. In this example, the container or device under test (201) is, for example, a 5/55/65 gallon drum. A telephoto lens (202) is also provided. The excitation laser (203), in a first example, is a diode-pumped solid-state laser housed in a TO-3 case having a wavelength of 1.54 μm, pulse energy of 100 μj, pulse width of 2 ns, peak power of 50 kW, and repetition rate of SS-10 Hz. In a second example, a diode-pumped solid-state laser is provided having a wavelength of 1.54 μm, pulse energy of 4 mJ, pulse width of 7 ns, and repetition rate of SS-10 Hz. The probe laser (204), for example, is a Fabry-Perot laser cavity having a single transverse mode of 130 mW in a wavelength range of 1550 nm with InGaAs laser diodes. In another example, a single transverse mode of 44 mW is provided in a wavelength range 1550 nm with InGaAsP/InP laser diodes.

The non-polarizing beam splitter (205), in a first example, has a BK7 grade A optical glass having a dimension tolerance of ±0.2 mm, flatness of ¼ @ 632.8 nm per 25 mm, surface quality of 60/40 scratches and dig, 50/50±5%, for random polarization, $T=(Ts+Tp)/2$, $R=(Rs+Rp)/2$, beam deviation <3 arc minutes, 20 mm. In a second example, it has a narrow band BK7 grade A optical glass, broadband SF5 optical glass, dimension tolerance of ±0.2 mm, flatness of ¼ @ 632.8 nm per 25 mm, surface quality of 60/40 scratches and dig, transmittance of 45%±5%, absorption <10%, and beam deviation <3 arc minutes.

The polarizing beam splitter (206) is preferably a narrow band BK7 grade A optical glass, broadband SF5 optical glass, dimension tolerance of ±0.2 mm, extinction ratio >100:1, flatness ¼ @ 632.8 nm per 25 mm, surface quality of 60/40 scratches and dig, principal transmittance Tp>95% and Ts<1%, principal reflectance Rs>99% and Rp<5%, and beam deviation <3 arc minutes. The polarizer (207) is preferably a linear NIR polarizer nominal 50% at 1550. Alternatively, the polarizer is a linear polarizer having an extinction ratio better than 10,000:1, high transmission, wide acceptance angle, and low wavefront distortion.

The retardation plate (208) preferably has dimensions 5 mm×5 mm, material: crystal quartz, substrate: BK-7, 2 mm thick, bonding: cement, wavelength: 1550 nm, coating: AR<0.5%. In a second example, the plate is a crystal quartz, having a dimension tolerance of +0.0, −0.2 mm, wavefront distortion <⅛ @ 632.8, retardation tolerance <1/500, parallelism <1 arc second, clear aperture >80%, surface quality 20/10 scratches and dig, and coating R<0.2% on both surfaces at central wavelength.

The photorefractive crystal (209), in a first example, is a CdTe, Ge crystal, germanium-doped to give a dark conductivity of $10^{-9}$ $\Omega cm^{-1}$ with dimensions 4 mm×5 mm×10 mm cut along [112], [111], and [110] directions, respectively, having faces parallel to [110] polished, faces parallel to [111] silvered. In a second example, a CdTe:V, crystal, vanadium-doped, is provided with dimensions 3 mm×3 mm×5 mm cut along [112], [111], and [110] directions, respectively, having the faces parallel to [110] polished, faces parallel to [111] silvered. In a third example, a GaAs crystal with no doping with dimensions 5 mm×5 mm×5 mm cut along [001], [110], and [110] directions, respectively, is provided that also has the faces parallel to [110] polished. The mirror (210), in a first example, is preferably BK7, Pyrex or UV fused silica, and has a dimension tolerance: +0.0, −0.2 mm, thickness tolerance: ±0.2 mm, clear aperture: >80%, flatness: 1/10 @ 633 nm, parallelism: <1 arc minute, surface quality: 20/10 (S/D), bevel (chamfer): 0.15~0.35 mm×45° face width×45°±15°, coating surface (S1): AOI=0°, R>99.8%, AOI=45°, R>99.5% (Rs>99.9%, Rp>99.2%). In a second example, the material is BK7 grade A optical glass, and the dimension tolerance is +0.0, −0.2 mm, thickness tolerance is ±0.2 mm, clear aperture is >80%, parallelism is <1 arc minute, surface quality is 60/40 (S/D), and bevel (chamfer) is 0.15~0.35 mm×45° face width× 45°±15°.

The photodiode (211), in a first example, is an InGaAs photodiode with a 15 MHz bandwidth, a wavelength of 1200-2600 nm, and a ɸ1 mm active area. In a second example, it is an InGaAs photodiode with a 1 GHz bandwidth, a wavelength of 1000-1600 nm, and a 75 μm active area.

Although the best mode contemplated by the inventors of carrying out the present invention is disclosed above, practice of the present invention is not limited thereto. It will be manifest that various additions, modifications, and rearrangements of the features of the present invention may be made without deviating from the spirit and scope of the underlying inventive concept.

Moreover, the individual components need not be formed in the disclosed shapes, or assembled in the disclosed configuration, but could be provided in virtually any shape, and assembled in virtually any configuration. Further, although the components are described herein as physically separate modules, it will be manifest that these may be integrated into the apparatus with which it is associated. Furthermore, all the disclosed features of each disclosed embodiment can be combined with, or substituted for, the disclosed features of every other disclosed embodiment except where such features are mutually exclusive.

We claim:

1. A portable non-contact sensor system, comprising:
   a laser generator subsystem configured to project a plurality of laser pulses at a surface of an object that is to be characterized, the laser pulses encoded with patterns, wherein the projected laser pulses generate ultrasonic waves within the object;
   a laser detector subsystem configured to project a laser beam at the surface and to receive return laser pulses from the object based on the generated ultrasonic waves;
   a beam steering subsystem operably associated with the laser generator subsystem and the laser detector subsystem;
   an analysis subsystem configured to analyze the received return pulses and characterize the object, the analysis subsystem including a microprocessor;
   a power management subsystem operably associated with the microprocessor;
   a user interface operably associated with the microprocessor; and
   a communications interface configured to enable communication between the sensor system and a device external to the sensor system,
   wherein the sensor system is configured to be hand-held.

2. The sensor system of claim 1, wherein the object comprises at least one of plastic, glass, a ferrous metal, and a non-ferrous metal.

3. The sensor system of claim 1, wherein the object comprises a container.

4. The sensor system of claim 3, wherein the container includes fluid.

5. The sensor system of claim 3, wherein the container is a closed container.

6. The sensor system of claim 5, wherein characterization of the object by the analysis subsystem includes characterization of contents of the container.

7. The sensor system of claim 5, wherein the object is at least one of a shipping container, a drum, a container of a chemical weapon, and a container of a biological weapon.

8. The sensor system of claim 1, wherein the object is organic.

9. The sensor system of claim 1, wherein the laser generator subsystem comprises a laser-diode pumped Q-switched laser.

10. The sensor system of claim 1, wherein the laser detector subsystem comprises a probe laser driven by a driver subsystem that employs feedback.

11. The sensor system of claim 1, wherein the laser detector subsystem comprises a probe laser having a wavelength range on the order of $10^3$ nanometers.

12. The sensor system of claim 1, wherein the laser detector subsystem comprises a probe laser and an adaptive interferometer.

13. The sensor system of claim 1, further comprising a database.

14. The sensor system of claim 1, wherein the communications interface is configured to enable communication between the sensor system and a database.

15. The sensor system of claim 1, wherein the analysis subsystem is configured to determine at least one of a speed of sound, a frequency response, and an attenuation response associated with the object.

16. The sensor system of claim 1, wherein the analysis subsystem is configured to characterize the object using spectral analysis.

17. The sensor system of claim 1, wherein the analysis subsystem is configured to detect presence of a defect or a contaminant.

18. The sensor system of claim 1, wherein the user interface includes a display.

19. The sensor system of claim 1, wherein the sensor system is configured to receive power from a battery.

20. The sensor system of claim 1, wherein the sensor system includes a housing having a handle portion grippable by a user.

21. A portable hand-held device for characterizing an object without contact, comprising:
    an excitation laser configured to project a plurality of laser pulses at a surface of an object that is to be characterized, wherein the projected laser pulses are encoded with patterns, and wherein the projected laser pulses generate ultrasonic waves within the object;
    a first driver configured to drive the excitation laser;
    a probe laser configured to project a probe laser beam, at least a portion of the probe laser beam being projected at the object;
    a second driver configured to drive the probe laser;
    a beam steering module operably associated with at least one of the excitation laser and the probe laser;
    an adaptive interferometer configured to receive return laser pulses from the object based on the generated ultrasonic waves;
    a microprocessor configured to analyze the received return pulses and characterize the object;
    a power management component operably associated with the microprocessor, wherein the hand-held device is configured to operate via power supplied by a battery;
    a user interface operably associated with the microprocessor and including a display;
    a communications interface configured to enable communication between the hand-held device and a second device external to the hand-held device; and
    a housing configured to house electronic and optical components of the hand-held device.

22. The hand-held device of claim 21, wherein the communications interface is configured to enable wireless communication.

23. The hand-held device of claim 21, wherein the power management component comprises a charging module configured to charge a battery.

24. The hand-held device of claim 21, wherein the housing is configured to house the display.

* * * * *